(12) United States Patent
Wei et al.

(10) Patent No.: US 10,945,793 B2
(45) Date of Patent: Mar. 16, 2021

(54) SYSTEM AND METHODS FOR PERCUTANEOUS TREATMENT PLANNING AND TREATMENT MONITORING

(71) Applicant: EDDA TECHNOLOGY, INC., Princeton, NJ (US)

(72) Inventors: Guo-Qing Wei, Plainsboro, NJ (US); Cheng-Chung Liang, West Windsor, NJ (US); Li Fan, Belle Mead, NJ (US); Jian-Zhong Qian, Princeton Junction, NJ (US); Xiaolan Zeng, Princeton, NJ (US)

(73) Assignee: EDDA TECHNOLOGY, INC., Princeton, NJ (US)

( * ) Notice: Subject to any disclaimer, the term of this patent is extended or adjusted under 35 U.S.C. 154(b) by 819 days.

(21) Appl. No.: 14/707,692

(22) Filed: May 8, 2015

(65) Prior Publication Data
US 2015/0320509 A1 Nov. 12, 2015

Related U.S. Application Data

(60) Provisional application No. 61/991,308, filed on May 9, 2014.

(51) Int. Cl.
*A61B 34/10* (2016.01)
*A61B 18/18* (2006.01)

(52) U.S. Cl.
CPC .......... *A61B 34/10* (2016.02); *A61B 18/1815* (2013.01); *A61B 2034/107* (2016.02)

(58) Field of Classification Search
CPC ..... A61B 90/00; A61B 34/10; A61B 19/5244; A61B 19/50; A61B 18/1815;
(Continued)

(56) References Cited

U.S. PATENT DOCUMENTS 4,962,754 A * 10/1990 Okazaki ................... A61B 8/14
600/439
6,138,045 A * 10/2000 Kupinski .............. G06T 7/0012
378/37
(Continued)

FOREIGN PATENT DOCUMENTS

| CN | 103209653 A | 7/2013 |
|---|---|---|
| CN | 103209653 A | 4/2017 |

(Continued)

OTHER PUBLICATIONS

International Preliminary Report on Patentability dated Nov. 15, 2016 in International Application PCT/US2015/030092.
(Continued)

*Primary Examiner* — Oommen Jacob
*Assistant Examiner* — Shahdeep Mohammed
(74) *Attorney, Agent, or Firm* — Pillsbury Winthrop Shaw Pittman LLP (57) ABSTRACT

The present teaching relates to surgical procedure assistance. In one example, a first image of a patient captured prior to a surgical procedure is received. A treatment plan is generated based on the first image. The treatment plan includes information related to one or more surgical instruments. A second image of the patient captured after the surgical procedure has been initiated is received. The treatment plan is dynamically adjusted based on a pose of any of the one or more surgical instruments identified from the second image. A third image of the patient captured after a lesion is treated by at least one of the surgical instruments based on the adjusted treatment plan is received. Whether a further treatment to the lesion is needed is determined based on the third image. Upon determining a further treatment is needed, an updated treatment plan is dynamically generated based on the third image.

22 Claims, 6 Drawing Sheets

(58) Field of Classification Search
CPC ...... A61B 2019/507; A61B 2019/5289; A61B 2019/505
See application file for complete search history.

(56) References Cited

U.S. PATENT DOCUMENTS

| | | | |
|---|---|---|---|
| 7,574,029 B2* | 8/2009 | Peterson | G06K 9/4638 382/130 |
| 7,672,705 B2 | 3/2010 | Lachaine | |
| 8,706,186 B2 | 4/2014 | Fichtinger et al. | |
| 2006/0036156 A1 | 2/2006 | Lachaine et al. | |
| 2007/0043285 A1* | 2/2007 | Schwartz | A61B 18/1492 600/407 |
| 2007/0116346 A1 | 5/2007 | Peterson et al. | |
| 2010/0185087 A1 | 7/2010 | Nields et al. | |
| 2010/0268223 A1 | 10/2010 | Coe et al. | |
| 2011/0288541 A1* | 11/2011 | Faure | A61B 18/1482 606/33 |
| 2014/0058387 A1* | 2/2014 | Kruecker | A61B 18/148 606/41 |
| 2014/0243737 A1* | 8/2014 | Erpelding | A61B 5/4839 604/22 |
| 2014/0303423 A1* | 10/2014 | Amthor | A61N 5/1027 600/8 |
| 2016/0051840 A1* | 2/2016 | Hårdemark | A61N 5/1031 600/1 |

FOREIGN PATENT DOCUMENTS

| | | | |
|---|---|---|---|
| EP | 2640292 A1 | 9/2013 | |
| WO | 2013057609 A1 | 4/2013 | |
| WO | WO 2014191064 A1 * | 12/2014 | ........... A61N 5/1031 |

OTHER PUBLICATIONS

Extended European Search Report dated Dec. 8, 2017 in European Application 15789210.0.
Office Action dated Jan. 4, 2019 in Chinese Application 201580024385.8.
Office Action dated Jul. 1, 2019 in Chinese Application 201580024385.8.

* cited by examiner

SYSTEM AND METHODS FOR PERCUTANEOUS TREATMENT PLANNING AND TREATMENT MONITORING

CROSS-REFERENCE TO RELATED APPLICATIONS

The present application claims priority to U.S. Provisional Application Ser. No. 61/991,308, filed May 9, 2014, entitled "System and Methods for Percutaneous Treatment Planning and Treatment Monitoring," which is incorporated herein by reference in its entirety.

BACKGROUND

Technical Field

The present teaching relates to surgical procedure assistance. More specifically, the present teaching is pertaining to percutaneous treatment planning and treatment monitoring for surgical procedures.

Discussion of Technical Background

In interventional procedures, one or more probes may be placed into the tumor. Through proper setting of the ablation device, such as the voltage and the duration in a microwave ablation device, the tumor tissue is killed by heating or freezing. Such interventional treatment procedures need a good treatment-planning method that can ensure proper tumor coverage with a safety margin and at the same time avoid the damage of critical organs. The planning method may provide an estimate of how many ablation probes may be needed for a tumor and how each probe may be positioned. But in the actual treatment, the planning may not be able to be exactly followed.

However, there is a lack of systems and methods for effectively and efficiently treatment planning and monitoring of interventional procedures. Therefore, there is a need to provide an improved solution to solve the above-mentioned problems.

SUMMARY

The present teaching relates to surgical procedure assistance. More specifically, the present teaching is pertaining to percutaneous treatment planning and treatment monitoring for surgical procedures.

In one example, a method implemented on a computing device having at least one processor, storage, and a communication platform connected to a network for surgical procedure assistance is disclosed. A first image of a patient captured prior to a surgical procedure is received. A treatment plan is generated based on the first image. The treatment plan includes information related to one or more surgical instruments. A second image of the patient captured after the surgical procedure has been initiated is received. The treatment plan is dynamically adjusted based on a pose of any of the one or more surgical instruments identified from the second image. A third image of the patient captured after a lesion is treated by at least one of the one or more surgical instruments based on the adjusted treatment plan is received. Whether a further treatment to the lesion is needed is determined based on the third image. Upon determining a further treatment is needed, an updated treatment plan is dynamically generated based on the third image.

In a different example, a system for surgical procedure assistance is disclosed. The system includes a preoperative planning unit, an intraoperative treatment plan adjusting unit, a treatment zone quantification unit, and a treatment plan supplementation unit. The preoperative planning unit is configured to receive a first image of a patient captured prior to a surgical procedure and generate a treatment plan based on the first image. The treatment plan includes information related to one or more surgical instruments. The intraoperative treatment plan adjusting unit is configured to receive a second image of the patient captured after the surgical procedure has been initiated, and dynamically adjust the treatment plan based on a pose of any of the one or more surgical instruments identified from the second image. The treatment zone quantification unit is configured to receive a third image of the patient captured after a lesion is treated by at least one of the one or more surgical instruments based on the adjusted treatment plan, and determine whether a further treatment to the lesion is needed based on the third image. The treatment plan supplementation unit is configured to, upon determining a further treatment is needed, dynamically generate an updated treatment plan based the third image.

Other concepts relate to software for implementing the present teaching on surgical procedure assistance. A software product, in accord with this concept, includes at least one non-transitory machine-readable medium and information carried by the medium. The information carried by the medium may be executable program code data, parameters in association with the executable program code, and/or information related to a user, a request, content, or information related to a social group, etc.

In one example, a non-transitory machine readable medium having information recorded thereon for surgical procedure assistance is disclosed. The recorded information, when read by the machine, causes the machine to perform a series of processes. A first image of a patient captured prior to a surgical procedure is received. A treatment plan is generated based on the first image. The treatment plan includes information related to one or more surgical instruments. A second image of the patient captured after the surgical procedure has been initiated is received. The treatment plan is dynamically adjusted based on a pose of any of the one or more surgical instruments identified from the second image. A third image of the patient captured after a lesion is treated by at least one of the one or more surgical instruments based on the adjusted treatment plan is received. Whether a further treatment to the lesion is needed is determined based on the third image. Upon determining a further treatment is needed, an updated treatment plan is dynamically generated based on the third image.

Additional features will be set forth in part in the description which follows, and in part will become apparent to those skilled in the art upon examination of the following and the accompanying drawings or may be learned by production or operation of the examples. The features of the present teachings may be realized and attained by practice or use of various aspects of the methodologies, instrumentalities and combinations set forth in the detailed examples discussed below.

BRIEF DESCRIPTION OF THE DRAWINGS

The methods, systems, and/or programming described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, systems, components, and/or circuitry have been described at a relatively high-level, without detail, in order to avoid unnecessarily obscuring aspects of the present teachings.

The present teaching is directed to methods, systems, and programming for percutaneous treatment planning, treatment plan adjustment, and treatment monitoring during surgical procedures. The method and system of the present teaching can automatically plan the needle path, estimate the coverage zone during the surgical procedures, and monitor the treatment effect to achieve safe and efficient treatment. The method and system of the present teaching are able to automatically adjust the plan during the procedure, so that the treatment zone corresponding to the actual probe position may be estimated before the ablation starts. After the procedure, the method and system of the present teaching can automatically compare the predicted treatment zone with the actual treatment zone to assess the treatment effect. In case there is an under-treated tumor region, additional probes may be placed for further treatment. For the newly placed probes, a combined treatment zone may be automatically estimated.

Figure 1:
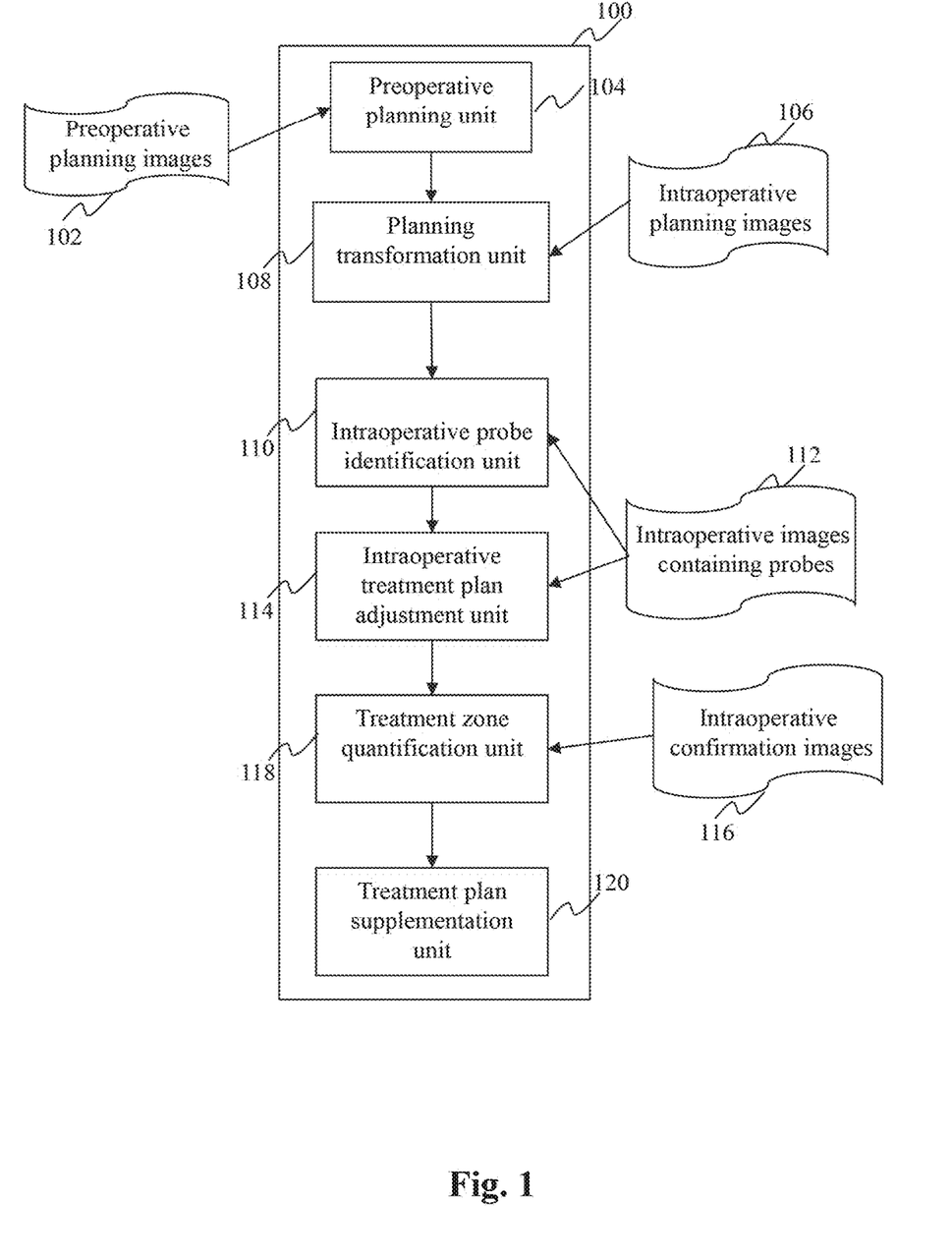
FIG. 1 shows an exemplary system diagram for treatment planning and treatment monitoring according to one embodiment of the present teaching.

The system 100 in this embodiment includes a preoperative planning unit 104, a planning transformation unit 108, an intraoperative probe identification unit 110, an intraoperative treatment plan adjustment unit 114, a treatment zone quantification unit 118, and a treatment plan supplementation unit 120. The treatment planning unit 104 takes preoperative planning images 102 to generate a 2D and/or 3D model of the anatomical structures of a patient. The model may include the lesion and a safety margin with respect to the lesion as well. A treatment plan may be generated through the treatment planning unit 104. This may include information related to the probes and the lesion. For example, the information may include the number of treatment probes, the planned treatment zone for each probe, the planned setting of each probe (e.g., ablation duration and power of an ablation probe), the planned path of each probe, the planned pose (position and orientation) of each probe, a planned coverage area of the lesion, etc. The planning transformation unit 108 may transform the preoperative plan onto the intraoperative images 106 acquired intra-operatively during the surgical procedures, e.g., in the operation room. The intraoperative probe identification unit 110 identifies probes in the intraoperative images 112. Based on the identified probe in the intraoperative images 112, a treatment plan adjustment unit 114 adjusts the treatment plan based on the actual probe pose identified from the intraoperative images 112. The treatment zone quantification unit 118 may quantify the actual treatment zone from the intraoperative confirmation images 116. Based on the quantification result, the treatment plan supplementation unit 120 may plan extra probe placement for further treatment of untreated lesion area. It is understood that although "probe" is described in the present teaching, the system and method disclosed in the present teaching can be applied to any suitable surgical instrument used in interventional procedures, such as but not limited to probes, needles, knifes, catheters, etc.

Figure 2A:
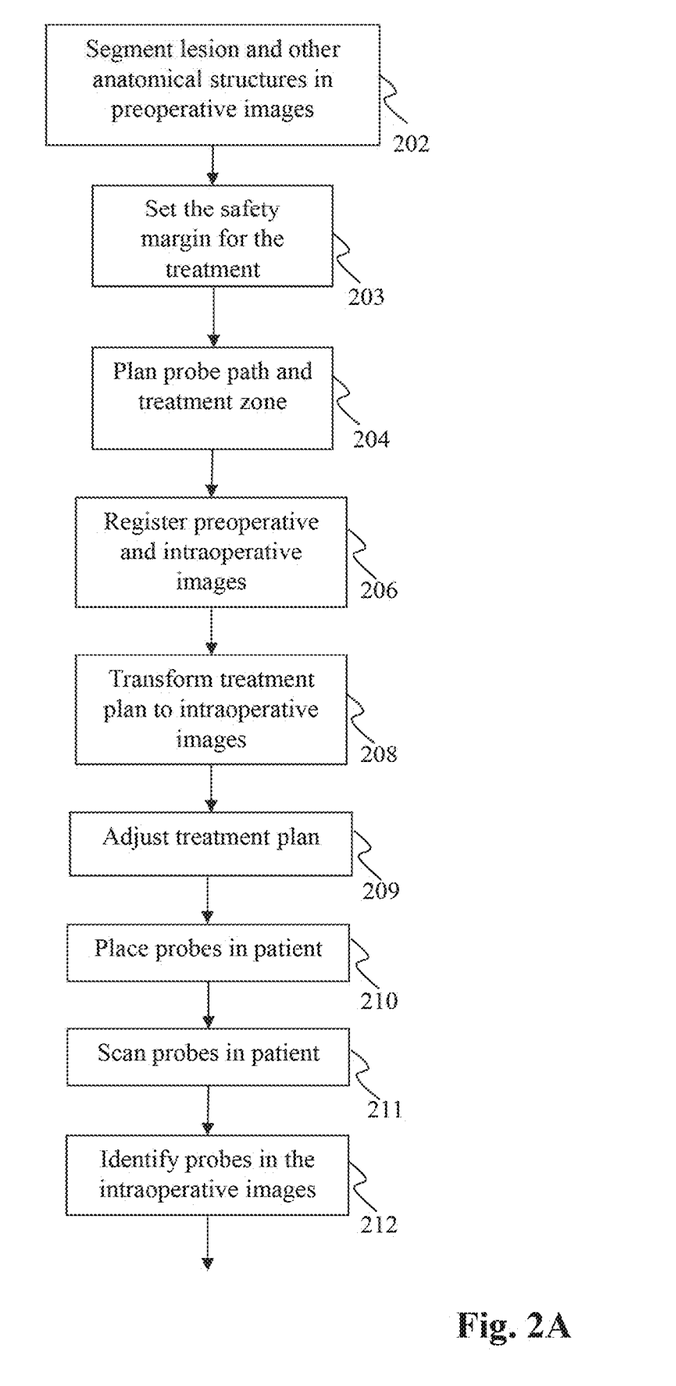
FIGS. 2A-2B show exemplary flow charts of treatment planning and treatment monitoring according to one embodiment of the present teaching.
Figure 2B:
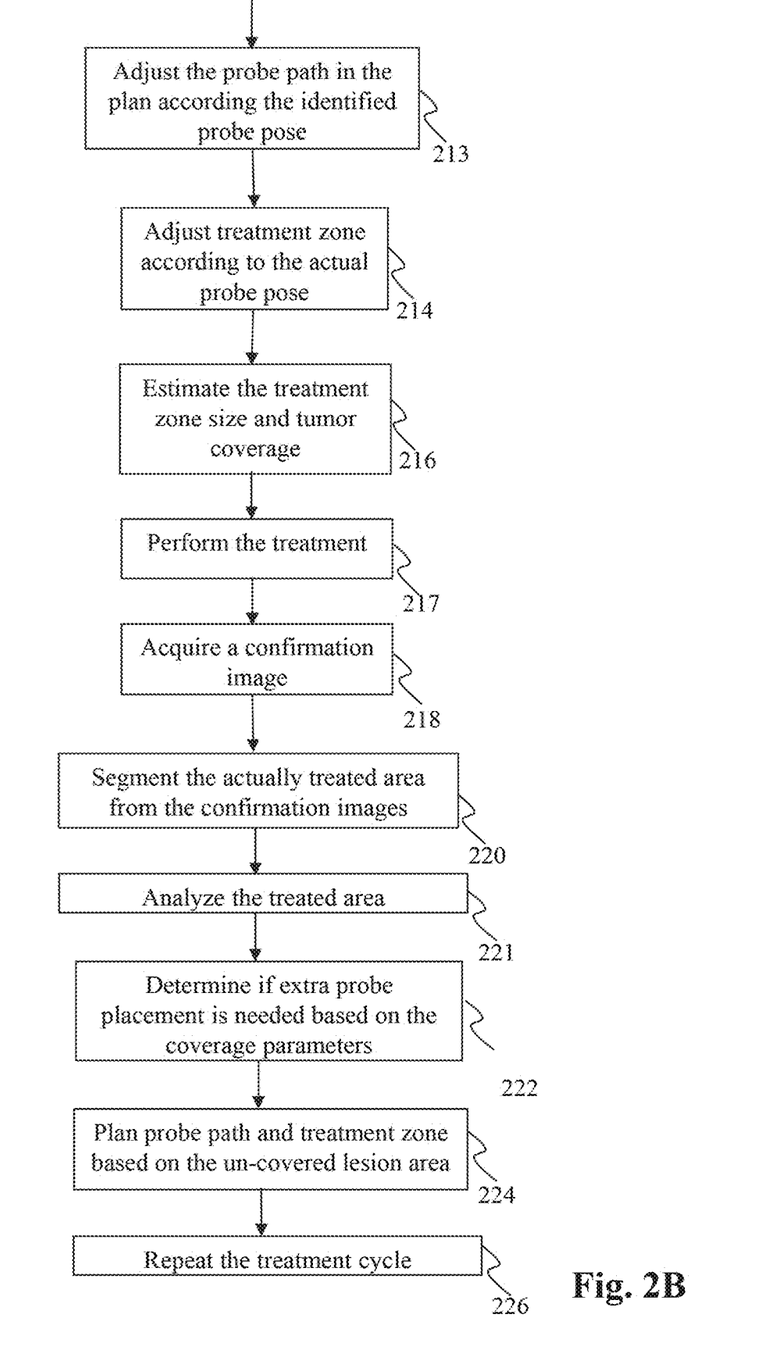

FIGS. 2A-2B are exemplary flow charts of the system 100, according to an embodiment of the present teaching. At 202, lesions and other anatomical structures may be segmented from preoperative images taken in any suitable modalities before the surgical procedure starts. At 203, a safety margin may be set for the lesion to be treated. The safety margin defines the total region to be treated, which may be larger than the lesion size. Based on the planned treatment zone, the number of probes, the probe path, and the treatment zone for each probe may be determined at 204. This may be performed automatically or interactively in 3D or 2D. At 206, the preoperative planning images may be registered with the intraoperative images taken in any suitable modalities during the surgical procedure. At 208, the treatment plan made based on the preoperative images may be transformed to the intraoperative image space. This may include, for example, skin entrance position for the probes, probe paths and planned treatment zone. Other anatomical structures, such as vascular structures and lesions, may be transformed from the preoperative images to the intraoperative images. Since intraoperative images are usually not contrast enhanced, such structures may not be clearly visible in the intraoperative images. The transformation of such anatomical structures may help better visualize critical anatomical structures.

At 209, the transformed treatment plan may be adjusted due to possible patient position change between the preoperative images and intraoperative images. For example, if the preoperative images were acquired in a supine view and the intraoperative images are acquired in a prone view, there may be possible organ's relative position change, which may render a treatment plan adjustment. This may include a change in probes' pose, the safety margin, and the treatment zone size. At 210, the physician performs the probe placement according to the adjusted treatment plan. After the probe(s) are placed into the patient's body at the targeted treatment position, at 211, a scan of the patient may be performed with probe(s) contained in the patient body. Then at 212, the probe(s) may be segmented from the newly acquired intraoperative images. This may be performed either automatically or interactively. At 213, the planned probe path for each probe may be adjusted automatically according to the identified probe location. The adjustment may align the planned pose (position and orientation) of the probe(s) to be the same as the actual probe pose (position and orientation). At 214, the treatment zone may be adjusted based on the actual probe pose. This may also include the change of pose (position and orientation) of the planned treatment zone to be aligned with the actual probe pose. At 216, the lesion coverage area may be re-estimated based on the adjusted treatment zone. The estimation may trigger a re-adjustment of the treatment zone size by changing the setting of the surgical instrument (e.g., ablation device). For example, the treatment zone may become larger than that was planned.

At 217, the physician may perform the treatment. After the treatment, a confirmation scan of the patient may be performed at 218 to obtain intraoperative confirmation images in any suitable modalities. At 220, the treated area may be segmented, either manually or automatically. At 221, the treatment effect may be quantified and analyzed. At 222, it may be determined whether an extra treatment may be needed. The analysis result from 221 may reveal that there may be untreated area within the planned treatment zone. At 224, based on the untreated area, new probe(s) may be planned. This may include an extra number of probes, the associated probe paths, the pose of each probe, and the treatment zone size of each probe. At 226, the treatment cycle may be restarted based on the plan. The same treatment monitoring method may then be applied.

Figure 3:
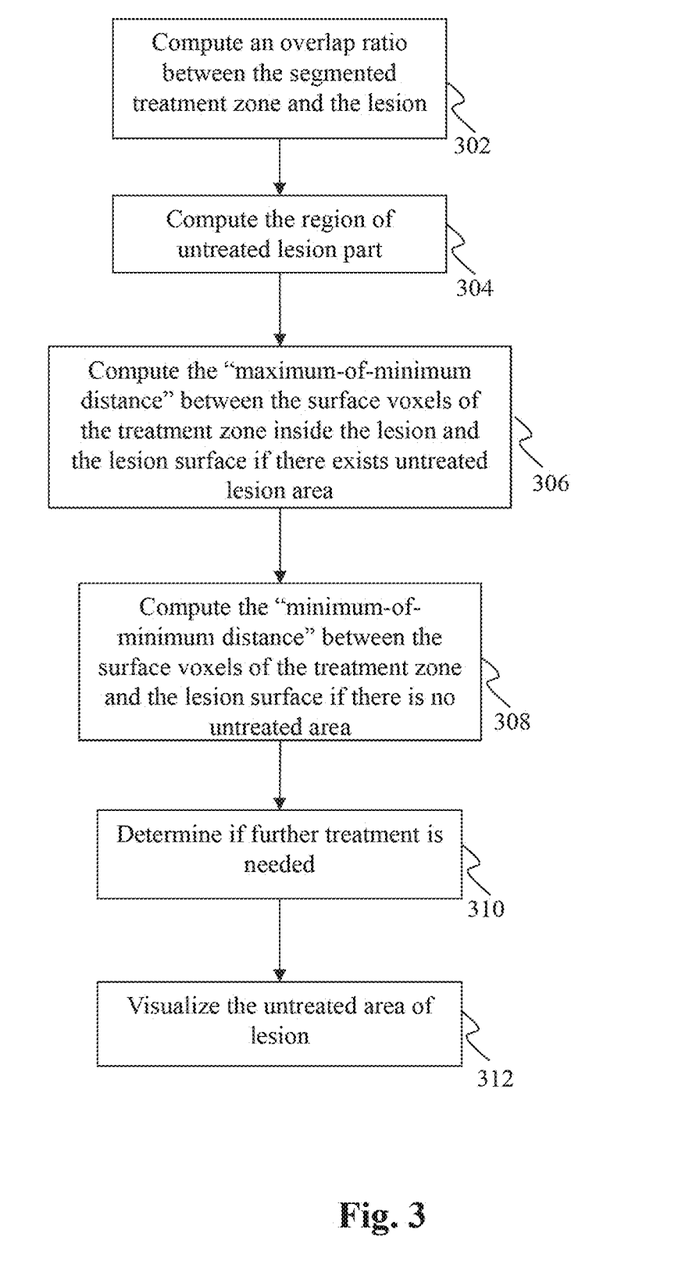
FIG. 3 shows an exemplary flow chart of treatment analysis according to one embodiment of the present teaching.
Figure 4A:
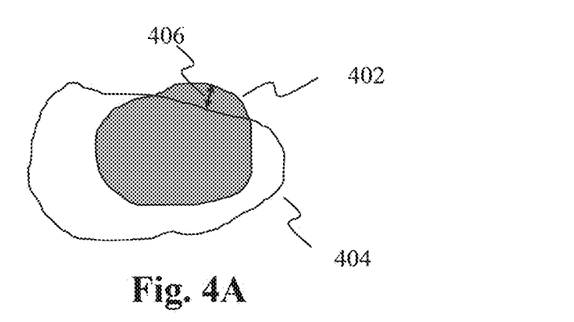
FIG. 4A shows an exemplary treated zone to compute "maximum-of-minimum distance," according to one embodiment of the present teaching.

FIG. 3 illustrates an exemplary flowchart of treatment analysis (e.g., 221 in FIG. 2B), according to an embodiment of the present teaching. At 302, an overlap ratio between the segmented treatment zone and the lesion may be computed. This ratio may be computed as the ratio (e.g., in percentage) of the volume of the overlap region divided by the lesion volume. For example, a value of 100% means that the lesion is completely covered by the treated region; a value less than 100% means partial coverage. At 304, the untreated lesion volume may be computed if the coverage is less than 100%. If there exists an untreated lesion area, a "maximum-of-minimum distance" between the surface of the treatment zone inside the lesion and the lesion surface may be computed. FIG. 4A illustrates one example of the "maximum-of-minimum distance," where 402 is the lesion, 404 is the treatment zone, and 406 is the "maximum-of-minimum distance" computed as the maximum value of the various distances between surface points of the treatment zone inside the lesion and the lesion surface. This value may be used to estimate how many probes may be used to treat the untreated area.

Figure 4B:
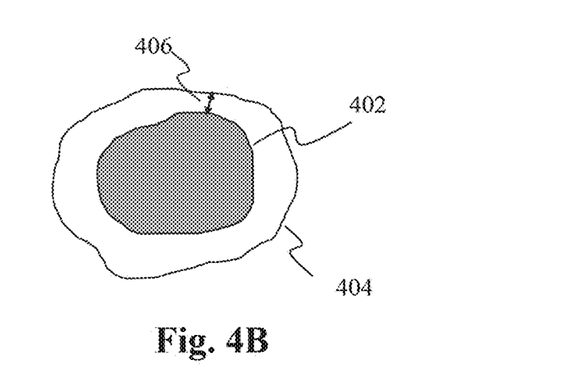
FIG. 4B shows an exemplary treated zone to compute "minimum-of-minimum distance," according to one embodiment of the present teaching.

If there is no untreated lesion area, a "minimum-of-minimum distance" may be computed, at 308, as the minimum value of the various distances between the voxels on the treatment zone and the lesion surface. FIG. 4B illustrates one example of the "minimum-of-minimum distance", where 402 is the lesion, 404 is the treatment zone, 406 is the "minimum-of-minimum distance." This value may be used to indicate the minimum value of the safety margin of the treatment. Based on the "maximum-of-minimum distance" and the "minimum-of-minimum distance," a decision may be made as to whether a further treatment is needed by placing extra probes, as well as how many probes may be needed.

Besides the quantitative measurements, the coverage may be examined visually by overlapping the planned treatment zone onto the intraoperative confirmation images. The planned treated zone and the actually treated zone may be visualized in a 2D or 3D space to examine the overlap. The "maximum-of-minimum" distance and "minimum-of-minimum" distance may be indicated on the intraoperative confirmation image. This may be performed at 312.

To implement various modules, units, and their functionalities described in the present disclosure, computer hardware platforms may be used as the hardware platform(s) for one or more of the elements described herein (e.g., the system 100 described with respect to FIGS. 1-4). The hardware elements, operating systems and programming languages of such computers are conventional in nature, and it is presumed that those skilled in the art are adequately familiar therewith to adapt those technologies to surgical procedure assistance as described herein. A computer with user interface elements may be used to implement a personal computer (PC) or other type of work station or terminal device, although a computer may also act as a server if appropriately programmed. It is believed that those skilled in the art are familiar with the structure, programming and general operation of such computer equipment and as a result the drawings should be self-explanatory.

Figure 5:
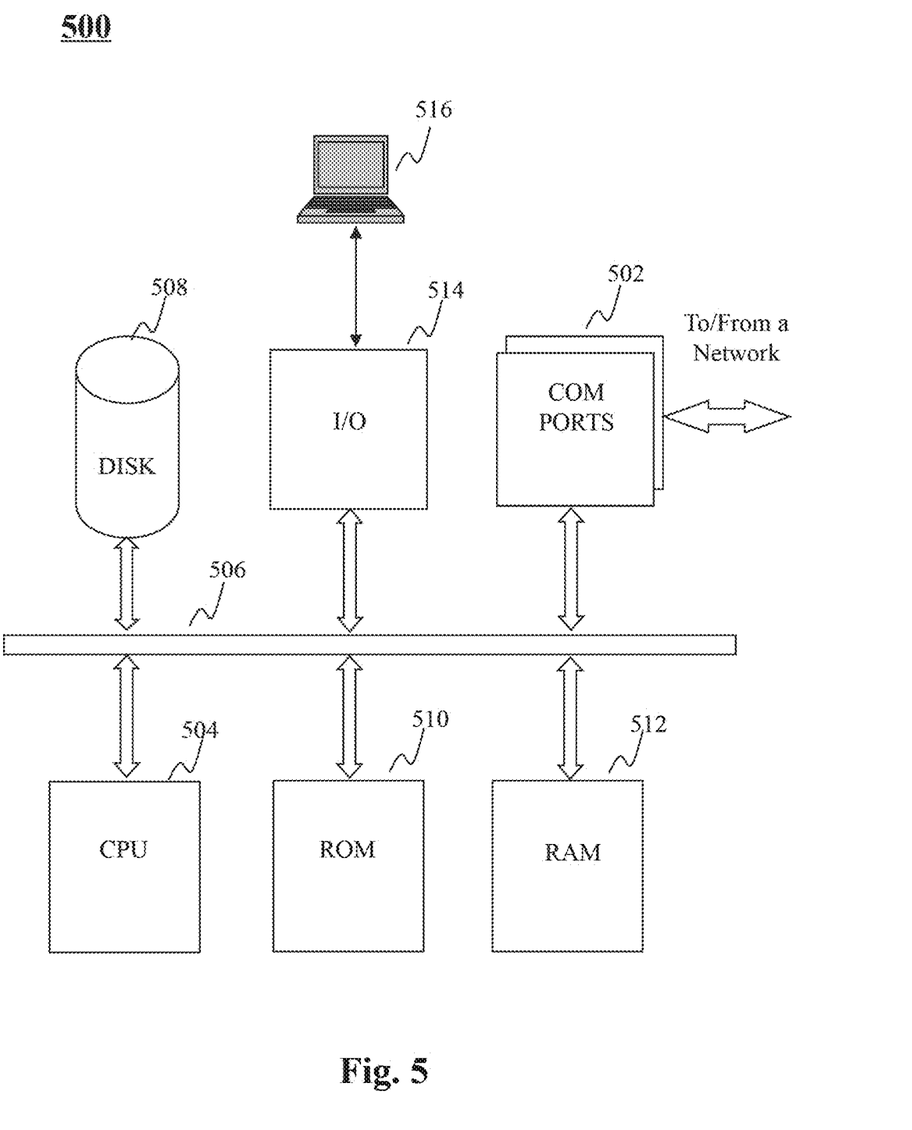
FIG. 5 depicts the architecture of a computer which can be used to implement a specialized system incorporating the present teaching.

FIG. 5 depicts the architecture of a computing device which can be used to realize a specialized system implementing the present teaching. Such a specialized system incorporating the present teaching has a functional block diagram illustration of a hardware platform which includes user interface elements. The computer may be a general purpose computer or a special purpose computer. Both can be used to implement a specialized system for the present teaching. This computer 500 may be used to implement any component of surgical procedure assistance techniques, as described herein. For example, the system 100 may be implemented on a computer such as computer 500, via its hardware, software program, firmware, or a combination thereof. Although only one such computer is shown, for convenience, the computer functions relating to surgical procedure assistance as described herein may be implemented in a distributed fashion on a number of similar platforms, to distribute the processing load.

The computer 500, for example, includes COM ports 502 connected to and from a network connected thereto to facilitate data communications. The computer 500 also includes a central processing unit (CPU) 504, in the form of one or more processors, for executing program instructions. The exemplary computer platform includes an internal communication bus 506, program storage and data storage of different forms, e.g., disk 508, read only memory (ROM) 510, or random access memory (RAM) 512, for various data files to be processed and/or communicated by the computer, as well as possibly program instructions to be executed by the CPU 504. The computer 500 also includes an I/O component 514, supporting input/output flows between the computer and other components therein such as user interface elements 516. The computer 500 may also receive programming and data via network communications.

Hence, aspects of the methods of surgical procedure assistance and/or other processes, as outlined above, may be embodied in programming Program aspects of the technology may be thought of as "products" or "articles of manufacture" typically in the form of executable code and/or associated data that is carried on or embodied in a type of machine readable medium. Tangible non-transitory "storage" type media include any or all of the memory or other storage for the computers, processors or the like, or associated modules thereof, such as various semiconductor memories, tape drives, disk drives and the like, which may provide storage at any time for the software programming.

All or portions of the software may at times be communicated through a network such as the Internet or various other telecommunication networks. Such communications, for example, may enable loading of the software from one computer or processor into another. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to tangible "storage" media, terms such as computer or machine "readable medium" refer to any medium that participates in providing instructions to a processor for execution.

Hence, a machine-readable medium may take many forms, including but not limited to, a tangible storage medium, a carrier wave medium or physical transmission medium. Non-volatile storage media include, for example, optical or magnetic disks, such as any of the storage devices in any computer(s) or the like, which may be used to implement the system or any of its components as shown in the drawings. Volatile storage media include dynamic memory, such as a main memory of such a computer platform. Tangible transmission media include coaxial cables; copper wire and fiber optics, including the wires that form a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a physical processor for execution.

Those skilled in the art will recognize that the present teachings are amenable to a variety of modifications and/or enhancements. For example, although the implementation of various components described above may be embodied in a hardware device, it may also be implemented as a software only solution—e.g., an installation on an existing server. In addition, the surgical procedure assistance system as disclosed herein may be implemented as a firmware, firmware/software combination, firmware/hardware combination, or a hardware/firmware/software combination.

While the foregoing has described what are considered to constitute the present teachings and/or other examples, it is understood that various modifications may be made thereto and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

We claim:

1. A method, implemented on a computing device having at least one processor, storage, and a communication platform capable of connecting to a network for surgical procedure assistance, comprising:
   receiving a first image of a patient captured prior to a surgical procedure;
   generating a treatment plan based on the first image, wherein the treatment plan includes information related to one or more surgical instruments;
   receiving a second image of the patient captured upon the surgical procedure being initiated;
   dynamically adjusting the treatment plan by registering the first image with the second image;
   receiving a third image of the patient captured after at least one of the one or more surgical instruments is placed into a lesion and before a treatment is initiated;
   identifying at least a pose of the one or more surgical instruments in the third image;
   adjusting the treatment plan by aligning a path associated with the one or more surgical instruments and a treatment zone based on the identified pose;
   estimating a size of the treatment zone before treatment is activated;
   acquiring a fourth image upon the treatment being performed;
   segmenting an actual treatment zone from the fourth image;
   computing, an overlap ratio based on the actual treatment zone and the lesion;
   calculating, in response to the overlap ratio between the actual treatment zone and the lesion satisfying a first condition, a first distance between a surface of the actual treatment zone and a surface of the lesion;
   calculating, in response to the overlap ratio between the actual treatment zone and the lesion satisfying a second condition, a second distance between the surface of the actual treatment zone and the surface of the lesion;
   determining, based on one of the first distance and the second distance, whether a further treatment to the lesion is required; and
   dynamically generating an updated treatment plan based on the further treatment to the lesion being determined.

2. The method of claim 1, wherein the step of determining comprises:
   automatically quantifying the actual treatment zone in relationship to the lesion.

3. The method of claim 1, wherein the overlap ratio is computed by dividing a volume of an overlap region between the actual treatment zone and the lesion by a volume of the lesion.

4. The method of claim 1, wherein generating the treatment plan comprises:
   segmenting the lesion and anatomical structures from the first image;
   determining a safety margin with respect to the lesion; and
   generating a model based on the lesion, anatomical structures, and safety margin.

5. The method of claim 1, wherein the information related to the one or more surgical instruments includes at least one of:
   a number of the one or more surgical instruments;
   a planned pose of any of the one or more surgical instruments;
   a planned path of any of the one or more surgical instruments;
   a planned treatment zone of any of the one or more surgical instruments; and
   a planned setting of any of the one or more surgical instruments.

6. The method of claim 1, wherein dynamically adjusting the treatment plan comprises adjusting at least one of the followings based on the pose of the corresponding surgical instrument identified from the third image:

a planned pose of any of the one or more surgical instruments;
a planned path of any of the one or more surgical instruments;
a planned treatment zone of any of the one or more surgical instruments; and
a planned setting of any of the one or more surgical instruments.

7. The method of claim 1, wherein the second image is captured before any one of the one or more surgical instruments is placed in the patient.

8. The method of claim 1, wherein the first condition corresponds to the overlap ratio being less than 100%.

9. The method of claim 1, wherein the second condition corresponds to the overlap ratio being equal to 100%.

10. The method of claim 1, wherein the step of determining whether a further treatment to the lesion is required further comprises:
determining, based on the first distance or the second distance, a number of additional probes to be placed at the lesion.

11. The method of claim 1, further comprising:
calculating the first distance based on a plurality of distances between the surface of the actual treatment zone inside the lesion and the surface of the lesion; and
calculating the second distance based on a plurality of distances between voxels on the actual treatment zone and the surface of the lesion.

12. The method of claim 11, further comprising:
providing the fourth image overlapped with at least one of:
the actual treatment zone,
the planned treatment zones, and
an indication of the first distance and/or the second distance.

13. A system for surgical procedure assistance, comprising:
a processor configured to:
receive a first image of a patient captured prior to a surgical procedure and generate a treatment plan based on the first image, wherein the treatment plan includes information related to one or more surgical instruments,
receive a second image of the patient captured upon the surgical procedure being initiated, and dynamically adjust the treatment plan by registering the first image with the second image,
receive a third image of the patient captured after at least one of the one or more surgical instruments is placed into a lesion and before a treatment is initiated,
identify at least a pose of the one or more surgical instruments in the third image,
adjust the treatment plan by aligning a path associated with the one or more surgical instruments and a treatment zone based on the identified pose,
estimate a size of the treatment zone before treatment is activated,
acquire a fourth image upon the treatment being performed,
segment an actual treatment zone from the fourth image,
compute, an overlap ratio based on the actual treatment zone and the lesion,
calculate, in response to the overlap ratio between the actual treatment zone and the lesion satisfying a first condition, a first distance between a surface of the actual treatment zone and a surface of the lesion,
calculate, in response to the overlap ratio between the actual treatment zone and the lesion satisfying a second condition, a second distance between the surface of the actual treatment zone and the surface of the lesion,
determine, based on one of the first distance and the second distance, whether a further treatment to the lesion is required, and
dynamically generate an updated treatment plan based on the further treatment to the lesion being determined.

14. The system of claim 13, wherein the processor is further configured to automatically quantify the actual treatment zone in relationship to the lesion.

15. The system of claim 13, wherein the overlap ratio is computed by dividing a volume of an overlap region between the actual treatment zone and the lesion by a volume of the lesion.

16. The system of claim 13, wherein the processor is further configured to:
segment the lesion and anatomical structures from the first image;
determine a safety margin with respect to the lesion; and
generate a model based on the lesion, anatomical structures, and safety margin.

17. The system of claim 13, wherein the information related to the one or more surgical instruments includes at least one of:
a number of the one or more surgical instruments;
a planned pose of any of the one or more surgical instruments;
a planned path of any of the one or more surgical instruments;
a planned treatment zone of any of the one or more surgical instruments; and
a planned setting of any of the one or more surgical instruments.

18. The system of claim 13, wherein the processor is configured to adjust at least one of the followings based on the pose of the corresponding surgical instrument identified from the third image:
a planned pose of any of the one or more surgical instruments;
a planned path of any of the one or more surgical instruments;
a planned treatment zone of any of the one or more surgical instruments; and
a planned setting of any of the one or more surgical instruments.

19. The system of claim 13, wherein the processor is further configured to:
calculate the first distance based on a plurality of distances between the surface of the actual treatment zone inside the lesion and the surface of the lesion; and
calculate the second distance based on a plurality of distances between voxels on the actual treatment zone and the surface of the lesion.

20. The system of claim 19, wherein the processor is further configured to provide the fourth image overlapped with at least one of:
the actual treatment zone,
the planned treatment zones, and
an indication of the first distance and/or the second distance.

21. A non-transitory machine readable medium having information recorded thereon for surgical procedure assistance, wherein the information, when read by a machine, causes the machine to perform the steps of:

receiving a first image of a patient captured prior to a surgical procedure;

generating a treatment plan based on the first image, wherein the treatment plan includes information related to one or more surgical instruments;

receiving a second image of the patient captured upon the surgical procedure being initiated;

dynamically adjusting the treatment plan by registering the first image with the second image;

receiving a third image of the patient captured after at least one of the one or more surgical instruments is placed into a lesion and before a treatment is initiated;

identifying at least a pose of the one or more surgical instruments in the third image;

adjusting the treatment plan by aligning a path associated with the one or more surgical instruments and a treatment zone based on the identified pose;

estimating a size of the treatment zone before treatment is activated;

acquiring a fourth image upon the treatment being performed;

segmenting an actual treatment zone from the fourth image;

computing, an overlap ratio based on the actual treatment zone and the lesion;

calculating, in response to the overlap ratio between the actual treatment zone and the lesion satisfying a first condition, a first distance between a surface of the actual treatment zone and a surface of the lesion;

calculating, in response to the overlap ratio between the actual treatment zone and the lesion satisfying a second condition, a second distance between the surface of the actual treatment zone and the surface of the lesion;

determining, based on one of the first distance and the second distance, whether a further treatment to the lesion is required; and dynamically generating an updated treatment plan based on the further treatment to the lesion being determined.

22. The medium of claim 21, wherein the step of determining comprises:

automatically quantifying the actual treatment zone in relationship to the lesion.

* * * * *